United States Patent [19]
Viegas et al.

[11] Patent Number: 6,136,334
[45] Date of Patent: *Oct. 24, 2000

[54] MEDICAL USES OF IN SITU FORMED GELS

[75] Inventors: Tacey X. Viegas, Birmingham, Ala.; Lorraine E. Reeve, Dexter; Raymond L. Henry, St. Clair Shores, both of Mich.

[73] Assignee: MDV Technologies, Inc., San Diego, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/330,618

[22] Filed: Jun. 11, 1999

Related U.S. Application Data

[63] Continuation of application No. 08/773,755, Dec. 23, 1996, Pat. No. 5,958,443, which is a continuation of application No. 08/174,101, Dec. 28, 1993, abandoned, which is a continuation of application No. 07/785,305, Oct. 30, 1991, Pat. No. 5,318,780.

[51] Int. Cl.[7] ................ A61K 31/74; A61K 31/785; A61K 31/765; A61K 9/50
[52] U.S. Cl. ............... 424/427; 424/78.04; 424/78.17; 424/78.18; 424/78.26; 424/78.37; 424/430; 424/436; 424/497; 514/772.7; 514/779; 514/912; 514/913; 514/914; 514/944; 514/966; 514/967; 523/122; 623/5
[58] Field of Search .................. 424/78.04, 78.17, 424/78.18, 78.26, 78.37, 427, 430, 436, 497; 514/772.7, 779, 912, 913, 914, 944, 966, 967; 523/122; 623/5

[56] References Cited

U.S. PATENT DOCUMENTS

| | | | |
|---|---|---|---|
| 3,590,125 | 10/1969 | Hymes | 424/78.38 |
| 3,640,741 | 2/1972 | Etes | 106/170 |
| 3,867,521 | 2/1972 | Miskel | 424/457 |
| 4,100,271 | 2/1976 | Krezanoski | 514/11 |
| 4,188,373 | 11/1977 | Krezanoski | 514/11 |
| 4,439,196 | 3/1984 | Higuchi | 604/890 |
| 4,474,751 | 10/1984 | Haslam et al. | 424/78 |
| 4,474,752 | 10/1984 | Haslam | 424/78 |
| 4,475,753 | 10/1984 | Haslam, et al. | 424/78 |
| 4,478,822 | 10/1984 | Haslam | 424/94.6 |
| 4,511,563 | 4/1985 | Schmolka | 514/162 |
| 4,540,407 | 9/1985 | Dunn | 604/292 |
| 4,570,626 | 2/1986 | Norris et al. | 128/132 |
| 4,767,619 | 8/1988 | Murray | 424/78 |
| 4,795,642 | 1/1989 | Cohen et al. | 424/455 |
| 4,856,513 | 8/1989 | Muller | 128/303.1 |
| 4,861,580 | 8/1989 | Janoff et al. | 424/1.1 |
| 4,861,760 | 8/1989 | Mazuel et al. | 514/54 |
| 4,879,109 | 11/1989 | Hunter | 514/723 |
| 4,883,660 | 11/1989 | Blackman et al. | 424/78 |
| 4,895,724 | 1/1990 | Cardinal et al. | 424/418 |
| 4,911,926 | 3/1990 | Henry et al. | 424/426 |
| 4,913,903 | 4/1990 | Sudmann et al. | 424/426 |
| 4,948,575 | 8/1990 | Cole et al. | 424/44 |
| 5,068,225 | 8/1990 | Pennell et al. | 514/57 |
| 5,071,644 | 12/1991 | Viegas et al. | 514/772.7 |
| 5,080,893 | 1/1992 | Goldberg et al. | 514/57 |
| 5,214,093 | 5/1993 | Nell et al. | 524/506 |
| 5,219,895 | 6/1993 | Kelman et al. | 522/68 |
| 5,279,611 | 1/1994 | McDonnell et al. | 606/4 |
| 5,369,131 | 11/1994 | Poli et al. | |
| 5,484,610 | 1/1996 | Bae | |

FOREIGN PATENT DOCUMENTS

| | | |
|---|---|---|
| 0274431A2 | 7/1988 | European Pat. Off. |
| 0386960 | 2/1990 | European Pat. Off. |
| 0126684B1 | 8/1991 | European Pat. Off. |
| 0455396A1 | 11/1991 | European Pat. Off. |
| 0517160 | 2/1992 | European Pat. Off. |
| 0227494B1 | 4/1992 | European Pat. Off. |
| 0551626A1 | 7/1993 | European Pat. Off. |
| 0598116A1 | 5/1994 | European Pat. Off. |
| 0694310A1 | 1/1996 | European Pat. Off. |
| 9004971 | 5/1990 | WIPO |
| 9403157 | 2/1994 | WIPO |
| 9414415 | 7/1994 | WIPO |
| 9509626 | 4/1995 | WIPO |
| 9524430 | 9/1995 | WIPO |
| 9620696 | 7/1996 | WIPO |

OTHER PUBLICATIONS

Amies, C.R. "Use of Topically Formed Calcium Alginate as a Depot Subst. in Active Immunisation" J. Path. Bact. 77:435–443 (1959).

Bodmeier, et al. "Spherical Agglomerates of Water–Insoluble Drugs" J. of Pharmaceutical Sciences 78(11):964–967 (1989).

Cotliar, et al. "Excimer Laser Radial Keratectomy" Ophthalmology 92: 206–208 (1985).

Fantes, et al. "Wound Healing After Excimer Laser Keratomileusis (Photorefractive Keratectomy) in Monkeys" Arch. Ophthalmol. 108:665–675 (1990).

Hanna, et al. "Excimer Laser Keratectomy for Myopia with a Rotating–Slit Delivery System" Arch. Ophthalmol. 106:245–250 (1988).

Hanna, et al. "Corneal Stromal Wound Healing in Rabbits After 193–nm Excimer Laser Surface Ablation" Arch. Ophthalmol. 107:895–901 (1989).

(List continued on next page.)

*Primary Examiner*—Carlos Azpuru
*Attorney, Agent, or Firm*—Pillsbury Madison & Sutro, LLP; W. Patrick Bengtsson; Nan Wu

[57] ABSTRACT

Balanced pH, hyperosmotic, hypoosmotic, or isoosmotic gels are ideal vehicles for drug delivery. They are especially suited for topical body cavity or injection application of drugs or diagnostic agents; for drug or diagnostic agent delivery to the eye of a mammal; as protective corneal shields; or as ablatable corneal masks useful in laser reprofiling of the cornea. The compositions without the addition of a drug or diagnostic agent are useful as medical devices, for instance, in separating surgically or otherwise injured tissue as a means of preventing adhesions.

8 Claims, No Drawings

OTHER PUBLICATIONS

Kim, et al. "Pluronic® Polyol: A Potential Alloplastic Keratorefractive Material" J. of Cataract Refractive Surgery 14:312–316 (1988).

Krueger, et al. "Quantitation of Corneal Ablation by Ultraviolet Laser Light" Arch. Ophthalmol. 103:1741–1742 (1985).

Marshall, et al. "An Ultrastructural Study of Corneal Incisions Induced by an Excimer Laser at 193 nm" Ophthalmology 92:749–758 (1985).

Pfister, et al. "Release Characteristics of Herbicides from Ca Alginate Gel Formulations" J. of Controlled Releases 3:229–233 (1986).

Poland, et al. "Clinical Uses of Collagen Shields" J. Cataract Refractive Surgery 14:489–491 (1988).

Puliafito, et al. "Excimer Laser Ablation of the Cornea and Lens. Experimental Studies" Ophthalmology 92:741–748 (1985).

Reidy, et al. "The Collagen Shield. A New Vehicle for Delivery of Cyclosporin A to the Eye" Cornea 9(3):196–199 (1990).

Search Results Dialog, Dec. 23, 1993.

Search Results Dialog, Dec. 29, 1993.

Shofner, et al. Ophthalmology Clinics of North America 2(1): 15–23 (1989).

Taylor, et al. "Human Excimer Laser Lamellar Keratectomy. A Clinical Study" Ophthalmology 96:654–664 (1989).

Trokel, et al. "Excimer Laser Surgery of the Cornea" Am. J. Ophthalmology 96:710–715 (1983).

MEDICAL USES OF IN SITU FORMED GELS

This is a continuation (MPEP 201.19) of National Appln. No. 08/773,755 filed Dec. 23, 1996 now U.S. Pat. No. 5,958,443, which is a continuation of Ser. No. 08/174,101, filed Dec. 28, 1993, now abandoned, which is a continuation of U.S. Ser. No. 07/785,305, filed Oct. 30, 1991, now U.S. Pat. No. 5,318,780, each of which are hereby incorporated by reference in their entireties.

BACKGROUND OF THE INVENTION

1. Field of the Invention

This invention relates to drug delivery system, the prevention of post-surgical adhesions, ophthalmic corneal protective devices, and a surgical device used in the correction, for instance, of corneal ulcers, irregularities, scarring, astigmatism, myopia, and hyperopia.

2. Description of the Prior Art

Over the years, methods have been developed to achieve the efficient delivery of a therapeutic drug to a mammalian body part requiring pharmaceutical treatment. Use of an aqueous liquid which can be applied at room temperature as a liquid but which forms a semisolid gel when warmed to body temperature has been utilized as a vehicle for drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC® polyols are used in aqueous compositions to provide thermally gelling aqueous systems. Adjusting the concentration of the polymer provides the desired sol-gel transition temperature, that is, the lower the concentration of polymer, the higher the sol-gel transition temperature, after crossing a critical concentration minimum, below which a gel will not form.

In U.S. Pat. No. 4,474,751; '752; '753; and 4,478,822 drug delivery systems are described which utilize thermosetting gels; the unique feature of these systems is that both the gel transition temperature and/or the rigidity of the gel can be modified by adjustment of the pH and/or the ionic strength, as well as by the concentration of the polymer.

Other patents disclosing pharmaceutical compositions which rely upon an aqueous gel composition as a vehicle for the application of the drug are U.S. Pat. Nos. 4,883,660; 4,767,619; 4,511,563; and 4,861,760. Thermosetting gel systems are also disclosed for application to injured mammalian tissues of the thoracic or peritoneal cavities in U.S. Pat. No. 4,911,926.

Ionic polysaccharides, have been used in the application of drugs by controlled release. such ionic polysaccharides as chitosan or sodium alginate are disclosed as useful in providing spherical agglomerates of water-insoluble drugs in the *Journal of Pharmaceutical Sciences* volume 78, number 11, November 1989, Bodmeier et al. Alginates have also been used as a depot substance in active immunization, as disclosed in the *Journal of Pathology and Bacteriology* volume 77, (1959), C. R. Amies. Calcium alginate gel formulations have also found use as a matrix material for the controlled release of herbicides, as disclosed in the *Journal of Controlled Release*, 3 (1986) pages 229–233, Pfister et al.

In U.S. Pat. No. 3,640,741, a molded plastic mass composed of the reaction product of a hydrophilic colloid and a cross-linking agent such as a liquid polyol, also containing an organic liquid medium such as glycerin, is disclosed as useful in the controlled release of medication or other additives. The hydrophilic colloid can be carboxymethyl cellulose gum or a natural alginate gum which is cross-linked with a polyol. The cross-linking reaction is accelerated in the presence of aluminum and calcium salts.

In U.S. Pat. No. 4,895,724, compositions are disclosed for the controlled release of pharmacological macromolecular compounds contained in a matrix of chitosan. Chitosan can be cross-linked utilizing aldehydes, epichlorohydrin, benzoquinone, etc.

In U.S. Pat. No. 4,795,642, there are disclosed gelatin-encapsulated, controlled-release compositions for release of pharmaceutical compositions, wherein the gelatin encloses a solid matrix formed by the cation-assisted gellation of a liquid filling composition incorporating a vegetable gum together with a pharmaceutically-active compound. The vegetable gums are disclosed as polysaccharide gums such as alginates which can be gelled utilizing a cationic gelling agent such as an alkaline earth metal cation.

While the prior art is silent with respect to aqueous drug delivery vehicles and isotonicity thereof, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or occular insertion for delivery of a drug or other beneficial substance. Since this drug delivery device relies on the permeability of the semipermeable membranes to control the rate of delivery of the drug, the drugs or other pharmaceutical preparations, by definition, are not isotonic with mammalian blood.

Corneal protective devices are needed in cases in which corneal injury occurs and the immobilization of the eye using an eye patch is not resorted to. Molded collagen shields have been developed for this use. These are often not satisfactory because they lack sufficient flexibility to adequately conform to the individual corneal curvature. Wetting a collagen shield will increase conformance of the shield to the cornea but fragmentation can occur upon exceeding the flexibility of the collagen shield. The clinical uses of collagen shields are disclosed by Poland et al. in *Journal of Cataract Refractive Survey*, Volume 14, September 1988, pages 489–491. The author describes the use of collagen shields immersed in tobramycin solution in order to rehydrate the collagen prior to use. These are described as useful following cataract extraction or in patients having nonsurgical epithelial healing problems. More rapid healing of epithelial defects after surgery resulted from the use of the collagen shield. Collagen shields have also been utilized as agents for the delivery of drugs to the cornea as disclosed in Reidy et al *Cornea*, in press, 1989 the Raven Press, Ltd., New York and Shofner et al, *Ophthalmology Clinics of North America*, Vol. 2, No. 1, March 1989, pages 15–23.

Refractive surgery has been promoted in the United States and Russia over the past few years but its acceptance has been limited because of the poor predictability of the final optical results which include resulting glare from incisions that encroach upon the optical zone. Techniques that rely upon the surgical production of corneal incisions have yielded inconsistent results because these surgical incisions in the cornea have been found to vary considerably in depth and length.

Laser keratectomy has been shown to be capable of yielding a more accurately controlled depth of corneal excision since each individual laser pulse excises a specific amount (0.2 to 10.0 um) of corneal tissue. Accordingly, the depth of excised tissue is in theory uniform and predictable, provided that the energy distribution is homogeneous across the laser beam. Since the primary locus of astigmatism is in the cornea, surgical intervention for astigmatism is more important than for the correction of other refractive errors, especially since spectacle or contact lens correction is of limited value in compensating for large astigmatic errors.

The excimer laser was introduced to ophthalmology in 1983 (Trokel, S., et al., "Excimer surgery of the cornea," Am. J. Ophthalmol. 96: 710–715, 1983). The depth of incision with short intense pulses permitted great precision to be achieved in tests on freshly enucleated cow eyes. The photochemical laser-tissue interaction is not thermal, permitting direct breaks of organic molecular bonds without involving optical breakdown in adjacent tissue. Early experimental results in rabbits revealed problems of 1) corneal stromal swelling, probably in response to disturbed water relationships due to compromise of the epithelial barrier and severing of the lamellae and (2) rearrangement of endothelial cells resulting from loss of contact inhibition (Marshall, J., et al., "An ultrastructural study of corneal incisions induced by an excimer laser at 193 nm", Ophthalmology 92: 749–758, 1985). Experiments with freshly enucleated human eyes indicated that flattening obtained by excimer laser ablation correlated with results of clinical scalpel radial keratotormy, but evaluation of the effects on wound healing and possible damage to adjacent structures was not addressed (Cotliar, A. M., et al., "Excimer laser radial keratotorny," Ophthalmology 92: 206–208, 1985). It was, however, suggested that this laser may become very useful in applications including penetrating and lamellar keratoplasty, keratomileusis, and epikeratophakia. Control of the area and depth Of pulses using photolithographed masks resulted in ability to produce narrow cuts (20 um) and at depths depending on pulse number (Puliafito, C. A., et al., "Excimer laser ablation of the cornea and lens", 5 Ophthalmology 92: 741–748, 1985). These controlled ablations had only very narrow bands of destruction at the adjacent edges. These studies led to the quantitation of laser ablation (Kruegar, R. R. and S. L. Trokell "Quantitation of corneal ablation by ultraviolet laser light", Arch. Ophthalmol. 103: 1741–1742, 1985). Excimer far UV radiation can be controlled to produce minimal adjacent tissue damage providing the angle and depth can be precisely controlled. The remaining problem of effects on healing could then be addressed.

Wound healing was assessed in rabbits following excimer laser surface ablation (Hanna, K. D., et al., "Corneal stromal wound healing in rabbits after 193 run excimer laser surface ablation", Arch. Ophthalmol. 107: 895–901, 1989). Healing appeared to be excellent except when over 85% to 90% of the corneal thickness had been cut. Endothelial cell disruption, junction separation and individual cell dropout occurred with corneal haze development with the deeper cuts. A delivery system designed to deliver predictable depths of cut is, therefore, essential. Similar findings were reported in studies on human blind eyes (Taylor, D. M., et al., "Human excimer laser lamellar Keratectomy", Ophthalmology 96: 654–664, 1989). Attention was directed to the challenges of improved procedures and equipment, the problems of individual variation, and the control of biologic responses to trauma before excimer laser lamellar keratectomy could become a clinically useful means of correcting refractive errors. In living monkey eyes, it was concluded that mild, typical wound healing occurred after excimer laser lamellar keratomileusis (Fantes, F. E., et &I, "Wound healing after excimer laser keratomileusis (photorefractive keratectorny) in monkeys", Arch. Ophthalmol. 108: 665–675, 5 1990). All corneas were epithelialized by 7 days. By 6 weeks, mild to moderate haze was apparent with clearing by 6 to 9 months. The epithelium was thickened at 21 days after ablation, but returned to normal by 3 months. Subepithelial fibroblasts were three times the density of normal keratocytes, but returned to nearly normal numbers by 9 months. One conclusion reached was that control of the contour and uniformity of the ablated surface is important for structural and biological responses of the cornea.

Review of the literature clearly reveals that far UV vaporization (ablation with an excimer laser at 193 nm, for example) is a feasible means to sculpture or reprofile the cornea to correct nearsightedness, farsightedness, astigmatism, corneal scars, corneal densities, etc. The healing appears to parallel or to be equal to healing after scalpel intervention, providing the proper guidelines for pulsing and duration are followed. There remains a need to control the contour and uniformity of the ablated surface. Such control will reduce the adverse structural and biological response of the cornea and insure that a desired corrective change results.

The use of a mask, of nearly identical optical density to the cornea, which can be preformed on the corneal surface so as to provide a smooth surface of exact contour and accurate dimensions would correct many of the problems that have prevented the precise control of the laser been during keratotorny. This mask would be required to withstand exposure to moist gases direct tangentally to the corneal surface throughout the duration of exposure to the laser to remove ablated debris. The modulation of the beam energy distribution of the laser in a controlled fashion should also be provided by such a corneal mask. The use of a smooth ablatable mask having a known contour and having the density of the cornea would aid in insuring accurate direction and depth of a tangental cut utilizing a laser beam. The ablatable mask of the invention provides such advantages.

Ionic polysaccharides have been used in the application of drugs by controlled release. Such ionic polysaccharides as chitosan or sodium alginate are disclosed as useful in providing spherical agglomerates of water-insoluble drugs in the Journal of Pharmaceutical Sciences, volume 78, number 11, November 1989, Bodmeier et al. Alginates have also been used as a depot substance in active immunization, as disclosed in the Journal of Pathology and Bacteriology, volume 77, (1959), C. R. Amies. Calcium alginate gel formulations have also found use as a matrix material for the controlled release of herbicides, as disclosed in the Journal of Controlled Release, 3 (1986) pages 229–233, Pfister et al. Alginates have also been used to form hydrogel foam wound dressings, as disclosed in U.S. Pat. No. 4,948,575.

SUMMARY OF THE INVENTION

Compositions and a process for drug or diagnostic agent delivery by topical, injection, or body cavity delivery are disclosed. The pharmaceutical compositions in one embodiment of the invention contain pharmacologically active medicaments which are useful in providing treatments to ophthalmic areas of the mammalian body requiring the controlled release application of a medicament or requiring the administration of a diagnostic agent. In addition, the compositions of the invention are useful, with or without the inclusion of a medicament, as injectable compositions for depot drug delivery, as a protective corneal shield, as a second skin for application to wounds, as an ablatable corneal mask in a laser keratectomy process or, as medical devices, for instance, in the separation of organs, injured in surgical procedures or otherwise, in order to prevent the formation of undesirable adhesions as part of the healing process.

The compositions of the invention provide a physiologically acceptable vehicle having a buffered pH and hypoosmotic, hyperosmotic, or isoosmotic characteristics. The pH and osmotic pressure is, preferably, made similar to bodily fluids, such as lacrimal tears. The pH and osmotic pressure of lacrimal tears is about pH 7.4 and 290 mOsm/kg. In addition, the pharmaceutical compositions are, optionally, sterilized so as to insure that the pharmaceutical compositions of the invention do not provide a source of infection.

Polyphase systems are also useful and may contain non-aqueous solutes, non-aqueous solvents, and other non-aqueous additives. Homogeneous, polyphase systems can contain such additives as water insoluble high molecular weight fatty acids and alcohols, fixed oils, volatile oils and waxes, mono-, di-, and triglycerides, and synthetic, water insoluble polymers without altering the functionality of the system.

The compositions of the invention in a preferred embodiment comprise aqueous mixtures of a film forming, water soluble polymer and an ionic polysaccharide, optionally containing a latent counter-ion to gel the polysaccharide upon release of the counter-ion. Alternatively, the compositions of the invention can comprise a two part aqueous system, one of which contains the ionic polysaccharide and film forming polymer and the other part containing an aqueous solution of a counter-ion.

The counter-ion can be provided in latent form by microencapsulation in a heat sensitive medium, for instance, the walls of the microcapsule can be made of mono-, di-, or tri-glycerides or other natural or synthetic heat sensitive polymer medium. Alternatively, ion exchange resins can be incorporated in the compositions of the invention so as to release the desired counter-ion upon contact with an environment opposite in pH to the pH of the ion exchange resin. The aqueous mixture can be delivered to the ophthalmic area of the mammalian body requiring treatment as a low viscosity liquid at ambient temperatures. Activation of the latent form of the counter-ion gels the aqueous mixture in situ. The two part system can be separately applied to gel the mixture in situ. Because the compositions of the invention are low viscosity liquids at ambient temperatures, they easily pass to various ophthalmic areas insuring maximum contact between exposed tissue and the compositions of the invention. The gel compositions of the invention can be either peeled away or allowed to be absorbed over time. The gels are gradually weakened upon exposure to mammalian body pH conditions.

The useful film forming polymers are, preferably, water soluble polymers such as those which have been used in ophthalmic applications. The hydroxyalkyl cellulosics and methyl celluloses, sodium hyaluronate, and polyvinyl alcohol are representative polymers which have been found useful in ophthalmic applications.

The useful ionic polysaccharides are natural polymers such as chitosan, gellan gum or alginates. Aqueous solutions of alginate ionic polysaccharides form gels upon contact with aqueous solutions of counter-ions such as calcium, strontium, aluminum, etc. Aqueous solutions of chitosan form gels upon contact with a metal tripolyphosphate counter-ion. The discovery forming the basis of this application is that when ionic polysaccharides are present in aqueous solutions in admixture with film forming polymers and a counter-ion, that such mixtures form useful gels. The osmolality of which can be calculated by assuming that the film forming polymer, if water soluble, does not contribute to the osmolality in the gel state.

DETAILED DESCRIPTION OF THE INVENTION

It has been found that aqueous pharmaceutical vehicles containing a film forming polymer and an ionic polysaccharide can be gelled and rendered resistant to shear thinning by contacting the mixture with a counter-ion. The gel compositions can be made isotonic or iso-osmotic and adjusted to the pH of mammalian body fluids, such as lacrimal tears. The pH and osmotic pressure of such bodily fluids are 7.4 and 290 mOsm/kg, respectively. It is advantageous to deliver a pharmacologically active medicament to an area of the mammalian body requiring pharmacological treatment under desired pH and osmotic pressure conditions which, for instance, match those of bodily fluids. Optionally, the pharmaceutical compositions of the invention can be provided in a sterile condition.

A complete listing of useful water soluble, film forming polymers is not possible. Representative useful polymers are the water soluble alkyl celluloses, i.e., methyl and ethyl cellulose; the hydroxyalkyl celluloses, i.e., hydroxypropylemethyl cellulose and hydroxyethyl cellulose; hyaluronic acid and water soluble salts thereof, i.e., sodium hyaluronate; chondroitin sulfate and water soluble salts thereof i.e., sodium chondroitin sulfate; polymers of acrylamide, acrylic acid, and polycyanoacrylates; polymers of methyl methacrylate and 2-hydroxyethyl methacrylate; polydextrose, cyclodextrin; polydextrin; maltodextrin, dextran; polydextrose; gelatin, collagen, natural gums, i.e., xanthan, locust bean, acacia, tragacanth, carrageenan, and agar; derivatives of polygalacturonic acid such as pectin; polyvinyl alcohol; polyvinyl pyrrolidone; polyethylene glycol; and polyethylene oxide. A preferred film forming agent is carboxymethyl ullulose and its sodium salt.

More complete descriptions of some of the preferred water soluble, film forming polymers are as follows. Cyclodextrin also known as cycloamylose is a cyclic oligosaccharide. Cyclodextrins are produced by the enzyme conversion of prehydrolized starch to a mixture of alpha, beta, and gamma cyclodextrins and some linear dextrins. The cyclodextrins are composed of glucose units linked together by alpha (1–4) glycosidic bonds.

Sodium hyaluronate also known as hyaluronic acid is composed of repeating units of sodium glucuronate and N-acetylglucosamine. Sodium hyaluronate was originally extracted from the comb of the rooster. Hyaluronic acid is a common biological agent present in a number of sources including the human umbilical cord. Sodium hyaluronate can also be manufactured by fermentation of a strain of streptococcus zooepidemicus.

Polydextrose is a randomly bonded condensation polymer of dextrose which is only partially metabolized by mammals. The polymer can contain a minor amount of bound sorbitol, citric acid, and glucose.

Chondroitin sulfate also known as sodium chondroitin sulfate is a mucopolysaccharide found in every part of human tissue, specifically cartilage, bones, tendons, ligaments, and vascular walls. This polysaccharide has been extracted and purified from the cartilage of sharks.

Carrageenan is a linear polysaccharide having repeating galactose units and 3,6 anhydrogalactose units, both of which can be sulfated or nonsulfated, joined by alternating 1–3 and beta 1–4 glycosidic linkages. Carrageenan is a hydrocolloid which is heat extracted from several species of red seaweed and irish moss.

Maltodextrins are water soluble glucose polymers which are formed by the reaction of starch with an acid and/or enzymes in the presence of water.

Further details of the composition and derivation of other useful water soluble, film forming polymers can be found in the HANDBOOK OF PHARMACEUTICAL EXCIPIENTS, published by the American Pharmaceutical Association Washington, D.C. copyright 1986, incorporated herein by reference.

The gel forming ionic polysaccharides found useful in the represent invention are hydrophilic colloidal materials and include the natural gums such as gellan gum, alginate gums, i.e., the ammonium and alkali metal salts of alginic acid and mixtures thereof. In addition, chitosan, which is the common name for deacetylated chitin is useful. Chitin is a natural product comprising poly-(N-acetyl-D-glucosamine). Gellan gum is produced from the fermentation of pseudomonas elodea to yield an extracellular heteropolysaccharide. The alginates and chitosan are available as dry powders from Protan, Inc., Commack, N.Y. Gellan gum is available from the Kelco Division of Merck & Co., Inc., San Diego, Calif.

Generally, the alginates can be any of the water-soluble alginates including the alkali metal alginates, such as sodium, potassium, lithium, rubidium and cesium salts of alginic acid, as well as the ammonium salt, and the soluble alginates of an organic base such as mono-, di-, or triethanolamine alginates, aniline alginates, and the like. Generally, about 0.2% to about 1% by weight and, preferably, about 0.5% to about 3.0% by weight of gellan, alginate or chitosan ionic polysaccharides, based upon the total weight of the composition, are used to obtain the gel compositions of the invention.

In general, the drug delivery composition of the invention will contain about 0.01% to about 60% by weight of medicament or pharmaceutical, about 1% to about 50% by weight of the water soluble, film forming polymer, together with the above amounts of ionic polysaccharide and the balance water. In special situations, these amounts of gel forming ionic polysaccharide and water soluble, film forming polymer may be varied to increase or decrease the gel properties.

Many polysaccharides may be used with the present invention to enhance the physical properties of the gel. For example, carboxymethylcellulose may reduce the rate of erosion of the polymer when compared to the polymer without the carboxymethylcellulose. In this regard, the carboxymethylcellulose competes with the polymer for the association of the water molecule, therefore, enhancing the stability of the gel to remain intact when in an aqueous environment.

When polysaccharides are utilized to enhance the physical properties of the gel, cross-linking of the polysaccharide is not necessary.

Polysaccharides that have not been crosslinked, and can be used to enhance the physical properties of the gel, include hydroxyalkyl cellulose and methylcellulose. More specifically, the useful polysaccharides are natural cellulose, hyaluronic acid and water soluble salts thereof, i.e. sodium hyaluronate, chondroitin sulfate and water soluble salts thereof, i.e. sodium chondroitin sulfate; polydextrose, cyclodextrin, polydextrin, maltodextrin, dextran; polydextrose; gelatin, collagen, natural gums, i.e. xanthan, locust bean, acacia, tragacanth, carrageenan, and agar, and derivatives of polygalacturonic acid such as pectin. A preferred polysaccharide is carboxymethylcellulose.

The drug delivery composition of the invention will contain about a 0.1% to about 25% by weight of the non-crosslinked polysaccharide to enhance the physical properties of the gel.

If an irreversible gel is required or an elastic gel, that is, one that retains its shape, cross-linking is required. Cross-linking is the physical, co-valent or ionic bonding of two or more molecules of the same polymer.

Any cross linking agent having more than one functional group wherein the function group is either chemical or ionic may be utilized to cross link the polysaccharides described above.

As known in the art, cross linking can ococur between molecules of similar polymers by physical reaction as long as appropriate functional groups are present on the polymers.

Useful counter-ions for gelling the gellan gum or alginate ionic polysaccharides in combination with the film forming, water soluble polymer compositions of the invention are cationic gelling agents, preferably, comprising a divalent or trivalent cation. Useful divalent cations include the alkaline earth metals, preferably, selected from the group consisting of calcium and strontium. Useful trivalent cations include aluminum. The most preferred counter-ions for gelling gellan gum or alginate ionic polysaccharides are contained in ionic compounds selected from pharmaceutically-acceptable gluconates, flourides, citrates, phosphates, tartrates, sulfates, acetates, borates, chlorides, and the like having alkaline earth metal cations such as calcium and strontium. Especially preferred counter-ion containing inorganic salts for use as ionic polysaccharide gelling agents include such inorganic salts as the chloride salts, such as strontium chloride, calcium chloride, and mixtures thereof. Generally, a molar ratio of counter-ion to gellan, 5 chitosan or alginate of about 1:1 to about 10:1, preferably, about 2:1 to about 5:1, and, most preferably, about 3:1 to about 5:1 is used.

While the counter-ion, such as calcium or other counter-ions may be obtained by contact of the compositions of the invention with bodily fluids, it is preferred that a counter-ion in latent form be used in combination with the gellan gum or alginate ionic polysaccharide and film forming, water soluble polymer compositions of the invention. Alternatively, a counter-ion can be combined with the ionic polysaccharide and water soluble, film forming polymer compositions of the invention utilizing a two part system in which the counter-ion is topically or otherwise applied to the compositions of the invention subsequent to their topical or other application.

Incorporation of the counter-ion in a latent form together with the ionic polysaccharide and film forming, water soluble polymer compositions of the invention may be accomplished by either encapsulating an aqueous solution of one of the counter-ion gelling agents, previously described above or by the incorporation of the counter-ion gelling agent into a matrix which provides for the controlled, slow-release of gelatin-encapsulated controlled release compositions disclosed in U.S. Pat. No. 4,795,642, incorporated herein by reference, disclose the preparation of a gelatin shell encapsulating a controlled release formulation in which the gelatin composition includes calcium chloride as the gelling agent. Alternatively, the counter-ion can be the incorporated as an aqueous solution of a cationic gelling agent encapsulated in a vesical composed, for instance, of alpha-tocopherol, as disclosed in U.S. Pat. No. 4,861,580, incorporated herein by reference.

Generally, aqueous compositions comprising chitosan can be gelled with multivalent anion gelling agents, preferably, comprising a metal polyphosphate, such as an alkali metal or ammonium polyphosphates, pyrophosphates, or metaphosphates. Representative metaphosphate, pyrophosphate, and polyphosphate gelling agents include sodium and potassium, polyphosphates, sodium and potassium pyrophosphates, sodium and potassium metaphosphates, and sodium and ammonium (mono-, di-, tri-) phosphates.

With specific reference to the use of the compositions of the invention as ophthalmic drug delivery compositions, laser ablatable shields, or corneal protective compositions, it is noted that, generally, for the avoidance of adverse physiological effects to the eye, it is desirable that the pH and osmolality of the pharmaceutical vehicle be matched to the pH and osmolality of the eye. In addition, it is noted that a large percentage of drugs administered to the eye are lost as a result of lacrimal drainage. This applies especially in situations in which a liquid composition containing a pharmacologically active medicament is applied to the cornea of the eye. Accordingly, in such cases, only a small fraction of the pharmaceutical composition administered to the eye remains in contact with the cornea for a few minutes and an even smaller fraction penetrates into the cornea. To overcome these disadvantages, it is known to use viscous solutions, gels, ointments, or solid eye implants containing pharmacologically active medicaments. While progress has been made in the delivery of drugs by the use of solid implants, many patients find it difficult to tolerate the introduction of the implants into the conjunctival areas.

To solve this problem, drug delivery vehicles which are liquid at room temperature and assume a semi-solid form at human body temperature have been proposed, such as those described in U.S. Pat. No. 4,188,373, which disclose the use of PLURONIC® polyols. In U.S. Pat. No. 4,861,760 and U.S. Pat. No. 4,474,751, ophthalmic drug delivery systems are disclosed which show liquid-gel phase transitions. In the '751 Patent, polymers are disclosed which are tetra substituted derivatives of ethylenediamine, propylenediamine, butylenediamine, pentylenediamine, or hexylenediamine. These are described as block copolymers of poly (oxypropylene) and poly(oxyethylene) of various chain lengths. These polymers were utilized as aqueous drug delivery vehicles contain from 10% to 50% by weight of polymer based on the weight of the total drug delivery vehicle. In the '760 Patent, the liquid-gel phase transition compositions for ophthalmological use contain polymers which form gels at concentrations 10–100 fold lower than those used in systems such as the '751 Patent, involving thermogelation. Accordingly, the drug delivery vehicles of the '760 Patent are said to be very well tolerated by the eye. The polymers utilized in the drug delivery vehicles of the '760 patent are described as polysaccharides obtained by fermentation of a microorganism.

The drug delivery vehicles and corneal protective shield compositions of the invention are an improvement over those compositions used in prior art methods of ophthalmological drug delivery in that the compositions can be not only optimized for physiological tolerance in the eye by formulating the vehicles useful as drug delivery compositions so as to have isoosmotic, hyperosmotic, and hypoosmotic characteristics in the gel state but are made more useful because of increased resistance to shear thinning, as the result of higher gel strength. These advantages are obtained by the incorporation of an ionic polysaccharide in admixture with a film forming, water soluble polymer. By matching the osmolality of the drug delivery compositions of the invention, for instance, to those of the lacrimal fluid of the eye, it is possible to eliminate burning or other discomfort upon application of the drug delivery vehicles of the invention to the eye. The gel compositions formed upon contact with a counter ion for the ionic polysaccharide allow retention of the gel at the desired locus for longer intervals thus increasing the efficiency of action of the delivered drug. Drugs or diagnostic agents which can be administered by means of the drug delivery vehicles according to the invention are, for example:

Antibacterial substances such as beta-lactam antibiotics, such as cefoxitin, n-formamidoylthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin and sulfonamides;

aminoglycoside antibiotics such as gentamycin, kanamycin, amikacin, sisomicin and tobramycin;

nalidixic acid and its analogs such as norfloxacin and the antimicrobial combination fluoroalanine/pentizidone, nitrofurazones and analogs thereof;

antihistaminics and decongestants such as pyrilamine, chlorpheniramine, tetrahydrazoline, antazoline and analogs thereof; mast-cell inhibitors of histamine release, such as cromolyn;

anti-inflammatories such as cortisone, hydrocortisone, hydrocortisone acetate, betamethasone, dexamethasone, dexamethasone sodium phosphate, prednisone, methylprednisolone, medrysone, fluorometholone, prednisolone, prednisolone sodium phosphate, triamcinolone, indainethacin, sulindac, its salts and its corresponding sulfides, and analogs thereof;

miotics and anticholinergics such as echothiophate, pilocarpine, physostigmine salicylate, diisopropylfluorophosphate, epinephrine, dipivaloylepinephrine, neostigmine echothiopate iodide, demecarim bromide, carbamoyl choline chloride, methacholine, bethanechol, and analogs thereof;

mydriatics such as atrophine, homatropine, scopolamine, hydroxyamphetamine, ephedrine, cocaine, tropicamide, phenylephrine, cyclopentolate, oxyphenonium, eucatropine, and analogs thereof;

Other drugs can be used in the treatment of conditions and lesions of the eyes such as:

antiglaucama drugs, for example, timalol, and especially its maleic salt and R-timolol and a combination of timolol or R-timolol with pilocarpine, as well as many other adrenergic agonists and/or antagonists: epinephrine and an epinephrine complex, or prodrugs such as bitartrate, borate, hydrochloride and dipivefrine derivatives; carbonic anhydrase inhibitors such as acetazolamide, dichlorphenamide, 2-(p-hydroxyphenyl)-thiothiophenesulfonamide, 6-hydroxy-2-benzothiazolesulfonamide, and 6-pivaloyloxy-2-benzothiazolesulfonamide;

antiparasitic compounds and/or anti-protozoal compounds such as ivermectin, pyrimethamine, trisulfapidimidine, clindamycin and corticosteroid preparations;

compounds having antiviral activity such as acyclovir, 5-iodo-2'-deoxyuridine (IDU), adenosine arabinoside (Ara-A), trifluorothymidine, interferon, and interferon-inducing agents such as poly I:C;

antifungal agents such as amphotericin B, nystatin, flucytosine, natamycin and miconazole;

anesthetic agents such as etidocaine cocaine, benoxinate, dibucaine hydrochloride, dyclonine hydrochloride, naepaine, phenacaine hydrochloride, piperocaine, pro-paracaine hydrochloride, tetracaine hydrochloride, hexylcaine, bupivacaine, lidocaine, mepivacaine and prilocaine;

ophthalmic diagnostic agents, such as:
(a) those used to examine the retina such as sodium fluorescein;
(b) those used to examine the conjunctiva, cornea and lacrimal apparatus, such as fluorescein and rose bengal; and
(c) those used to examine abnormal pupillary responses such as methacholine, cocaine, adrenaline, atropine, hydroxyamphetamine and pilocarpine;

ophthalmic agents used as adjuncts in surgery, such as alpha-chymotrypsin and hyaluronidase;

chelating agents such as ethylenediaminetetraacetic acid (EDTA) and deferoxamine;

immunosuppressants and anti-metabolites such as methotrexate, cyclophosphamide, 6-mercaptopurine and azathioprine and combinations of the compounds mentioned above, such as antibiotics/antiinflammatories combinations such as the combination of neomycin sulfate and dexamethasone sodium phosphate and combinations concomitantly used for treating glaucoma, for example, a combination of timolol maleate and aceclidine.

In general the drug delivery composition of the present invention will contain from about 0.01% to about 60% by weight of the medicament or pharmaceutical, from about 1% to about 50% of the polymer, the above amounts of ionic polysaccharide, and the balance water. In special situations, however, the amounts may be varied to increase or decrease the dosage schedule.

If desired, the ophthalmic drug delivery vehicle, laser ablatable corneal mask, and corneal protective compositions of the invention may also contain preservatives, cosolvents, suspending agents, viscosity enhancing agents, ionic-strength and osmolality adjustors and other excipients in addition to the medicament and buffering agents. Suitable water soluble preservatives which may be employed in the inventive drug delivery vehicle are sodium bisulfite, sodium thiosulfate, is ascorbate, benzalkonilirn chloride, chlorabutanol, thimerosal, phenylmercuricborate, parabens, enzylalcohol phenylethanol and others. These agents may be present, generally, in amounts of about 0.001% to about 5% by weight and, preferably, in the amount of about 0.01 to about 2% by weight.

Suitable water soluble buffering agents are alkali or alkali earth carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such the buffering agent can be as much as 5% on a weight basis of the total composition.

Representative buffering agents or salts useful in maintaining the pH at about 7.4±0.2 are alkali or alkali earth carbonates, chlorides, sulfates, phosphates, bicarbonates, citrates, borates, acetates and succinates. Representative preservatives are sodium bisulfite, sodium thiosulfate, ascorbate, benzalkonium chloride, chlorobutanol, thimerosal, phenylmercuric borate, parabens, benzylalcohol and phenylethanol.

The corneal mask compositions of the invention are an improvement over the prior art thermo-reversible gels containing a polyoxyalkylene polymer as the sole polymer, in that the compositions of the invention provide greater gel strength because they are more resistant to shear thinning and are characterized as thermally-irreversible. These advantages are obtained by the incorporation of an ionic polysaccharide in admixture with a water soluble, film forming polymer. They can be optimized for optimum physiological tolerance in the eye by formulating the compositions so as to have a neutral pH and isotonic characteristics. These former advantages are obtained by the incorporation of an ionic polysaccharide in admixture with a water soluble, film forming polymer. By matching the osmolality and pH of the laser ablatable corneal mask compositions of the invention to those of the lacrimal fluid of the eye, it is possible to eliminate burning or other discomfort upon application of the corneal mask of the invention to the eye. The higher gel strength compositions upon contact with a counter-ion allow retention of the gel as an in situ formed corneal mask for long intervals.

The preparation of the drug delivery compositions, corneal protective compositions, and ablative corneal shield compositions of the invention is described below. The Examples which follow were prepared, generally, in accordance with the following preparation procedure. A mixture of a water soluble, film forming polymer and ionic polysaccharide is stirred or shaken in admixture with the aqueous buffer solution to bring about a more rapid solution of the polymer. The pharmacologically active medicaments and various additives such as salts and preservatives can subsequently be added and dissolved. In some instances the pharmacologically active substance must be suspended since it is insoluble in water. The pH of 7.4 1 0.2 is obtained by of appropriate buffering agents.

The following Examples illustrate the various aspects of the invention but are not intended to limit its scope. Where not otherwise specified throughout this specification and claims, temperatures are given in degrees centigrade and parts, percentages, and proportions are by weight.

EXAMPLE 1

In this Example there is described a composition of the invention suitable for ophthalmic use as a laser ablatable corneal mask or protective corneal shield. The is composition was characterized as iso-osmotic and neutral I n pH. An aqueous solution was made by dissolving the hydroxypropyl methyl cellulose in aqueous buffer solution together with the sodium alginate. The hydroxypropyl methyl cellulose was characterized as grade F50LV Premium, obtained from The Dow Chemical Company. The sodium alginate, characterized as high viscosity grade HF 120 was obtained from Protan, Inc. The proportions of ingredients in percent by weight are as follows:

| | |
|---|---|
| Hydroxypropyl methyl cellulose | 2.0 |
| Sodium Alginate, high viscosity | 1.0 |
| Glycerin | 0.25 |
| Boric acid-sodium borate buffer | 96.75 |

The boric acid-sodium borate buffer was prepared as follows: In a two liter volumetric flask, 24.7 grams of boric acid and 3.8 grams of sodium borate decahydrate were dissolved in two liters of purified water, USP. The formulation of this Example had a measured pH of 7.2 and an osmolality of 277 mOsm/Kg. A small amount of the formulation was placed on a glass slide and evenly spread so as to create a thin film. The film was subsequently sprayed with an aqueous solution of calcium chloride having a concentration of 21 to about 5% by weight. The film was characterized as strong, transparent, and resembled a thin, soft hydrophilic corneal contact lens which would be useful as a protective corneal mask or as an ablatable mask useful in laser keratectomy.

The product was further characterized by measuring the average penetration in millimeters determined using a Precision Penetrometer with a ¼ size (9.38 grams, ASTM D-1043) cone and plunger. The penetration of the aqueous solution of polymers prepared above was greater than 20 mm. Subsequent to treatment of this solution with a few drops of a 2%–5% by weight aqueous solution of calcium chloride, a gel was formed in which the penetration was reduced to 5 mm.

EXAMPLES 2 AND 3

In these Examples there are described compositions of the invention for ophthalmic use as a corneal protective mask or as a laser ablatable corneal mask. Utilizing the same procedure as described in Example 1, an aqueous composition containing sodium hyaluronate and sodium alginate was prepared in two separate compositions. Sodium hyaluronate is commercially available from Meiji Seika Inc. Example 2 was hypoosmotic having an osmotic pressure of 249 mOSM/Kg and Example 3 was hyperosmotic having an osmotic pressure of 319 mosm/Kg. Both compositions were characterized as neutral in pH. The formulations have the following proportions by weight:

|  | Example 2 | Example 3 |
| --- | --- | --- |
| Sodium hyaluronate | 1.0 | 1.0 |
| Sodium alginate, high viscosity | 1.0 | 1.0 |
| Glycerin | . | 0.5 |
| Boric acid-sodium borate buffer | 98.0 | 97.5 |

These compositions were evaluated as described in Example 1 by spreading a small amount of the formulation on a glass slide and subsequently spraying the coated slide with a 5% by weight aqueous solution of calcium chloride. Similar strong, transparent, soft films were obtained which would be useful as a protective corneal shield or as a laser ablatable corneal mask.

Example 3 was further characterized by measuring the average penetration in millimeters determined using a Precision Penetrometer with a ¼ size (9–38 grams, ASTM D-1043) cone and plunger. The penetration of the aqueous solution of polymers prepared above was greater than 20 mm. Subsequent to treatment of this solution with a few drops of a 2%–5% by weight aqueous solution of calcium chloride, a gel was formed in which the penetration was reduced to 5.9 mm.

EXAMPLE 4

In this Example there is described a composition of the invention for ophthalmic use as a protective corneal shield or a laser ablatable corneal mask. An aqueous mixture comprising polyvinyl pyrrolidone and sodium alginate, high viscosity was prepared as follows: The percentages below are by weight.

| Polyvinyl pyrrolidone | 0.8 |
| --- | --- |
| Sodium alginate, high viscosity | 1.0 |
| Glycerin | 0.3 |
| Boric acid-sodium borate buffer | 97.9 |

The composition was characterized as neutral in pH having a pH of 7.2. The composition was hypoosmotic having an osmolality of 270 mOsm/Kg.

The product was further characterized by measuring the average penetration in millimeters determined using a Precision Penetrometer with a ¼ size (9.38 grams, ASTM D-1043) cone and plunger. The penetration of the aqueous solution of polymers prepared above was greater than 20 mm. Subsequent to treatment of this solution with a few drops of a 5% by weight aqueous solution of calcium chloride, a gel was formed in which the penetration was reduced to 4.1 mm.

EXAMPLE 5

In this Example there is described a composition of the invention for ophthalmic use as a laser ablatable mask or as a protective corneal shield. In accordance with the procedure of Example 1, chondroitin sulfate and sodium alginate were prepared as an aqueous solution utilizing the percentages by weight indicated below.

| Sodium Chondroitin sulfate | 2.0 |
| --- | --- |
| Sodium alginate, high viscosity | 1.0 |
| Glycerin | 0.3 |
| Boric acid-sodium borate buffer | 96.7 |

The aqueous solution was characterized as neutral in pH having a pH of 7.0. The aqueous solution was hyperosmotic having a measured osmolality of 354 mOsm/Kg. The penetration utilizing a Precision Penetrometer with a ¼ size cone, as described above, was greater than 20 mm prior to treatment with a few drops of a 2%–5% aqueous solution of calcium chloride. Subsequent to treatment with the aqueous calcium chloride solution, a gel was formed in which the penetration was reduced to 5.1 mm.

EXAMPLES 6–10

Ion exchange resin beads sold under the trade name Duolite were treated so as to incorporate calcium by first treating a 30 gram sample of the ion exchange resin with a solution of 0.1 molar hydrochloric acid so as to allow for the exchange of protons for sodium. After three washings with 0.1 molar hydrochloric acid, the beads were washed with water and then washed twice with a 2% aqueous solution of calcium chloride. Each of the washing steps took place over a period of 16 hours (overnight). The beads were thereafter filtered and washed with water utilizing coarse filter paper and a Buchner glass filter assembly. The beads were then left overnight in a desiccator to dry. The dried beads of ion exchange resin which were obtained are utilized in the amount of 2 grams to fill a first compartment (close to the needle of the syringe) of a glass syringe utilized to apply liquids and dry materials. The syringe is sold under the tradename Hypak. Into the second compartment of the syringe, there is placed successively the solutions of Examples 1–5. Pushing the plunger of the syringe forward results in mixing the solution of Examples 1–5 with the ion exchange beads. After 5 to 10 minutes subsequent to mixing, the mixture is expelled from the syringe. After an additional 15 minutes the expelled material forms (without drying) a strong, transparent gel on the substrate on which it is expelled.

EXAMPLES 11–15

These examples describe the successive application of an aqueous solution of Examples 1 and 3–5 to the cornea of a rabbit eye and the conversion of the aqueous liquid to a gel by the application of a 10% calcium chloride solution having a pH of 6.9. The calcium chloride solution is applied to the concave surface of a contact lens prior to contacting the surface of the aqueous liquid coating applied upon the cornea of the rabbit eye. After applying the compositions of Examples 1 and 3–5 to the cornea of a rabbit while placed under general anesthesia, a liquid coating is formed upon the cornea. Subsequently, a 10% aqueous solution of calcium chloride is applied to the concave surface of a hard contact lens and the contact lens is placed over the coating on the cornea of the rabbit eye. The time required for the formation of a gel is less than 5 minutes. Thereafter, the contact lens is removed to expose a perfectly smooth and optically clear gelled surface of the composition of Examples I and 3–5. Excimer laser keratectomy is thereafter performed utilizing an argon fluoride excimer laser (193 nm). Further details of the excimer laser keratectomey process can be found in *Archives of Ophthalmology*, Vol. 106, Feb., 1988, entitled "Excimer Laser Keratectomy with a Rotating-slit Delivery System", Hanna et al, incorporated herein by reference.

EXAMPLES 16–18

These Examples describe drug compositions of the invention suitable for ophthalmic use in comparison with Control Examples in in-vitro tests for drug release.

EXAMPLE 16 CONTROL

Forming no part of this invention

|  | Percentage by weight |
|---|---|
| Timolol maleate | 0.50 |
| Poloxamer 407 | 16.00 |
| Sodium phosphate, monobasic, monohydrate | 0.15 |
| Sodium phosphate, dibasic | 0.63 |
| Glycerin | 0.75 |
| Sterile water | 81.97 |

An eye drop or medicated contact lens composition was prepared using a suitable glass container in which the sodium phosphate salts and glycerin were dissolved in sterile water. The polymer was next mixed with the buffer solution at 65° C. for 1 hour, followed by a further 2–3 hours in cold conditions. To a fixed weight of the polymer solution was added and dissolved, an accurate amount of timolol maleate (Huhtamaki OY Pharmaceuticals, Turku, Finland) to make a 0.5% w/w concentration.

EXAMPLE 17 CONTROL

Forming no part of this invention

|  | Percentage by Weight |
|---|---|
| Timolol maleate | 0.50 |
| Poloxamer | 17.00 |
| Sodium alginate, high viscosity | 1.50 |
| Sodium borate, decahydrate | 0.16 |
| Boric acid | 1.00 |
| Glycerin | 0.30 |
| Sterile water | 81.27 |

A medicated contact lens was prepared using a suitable glass container in which the sodium borate, boric acid and glycerin were dissolved in sterile water. Sodium alginate was sprinkled in with stirring to form a uniform paste. The polymer was next mixed with this mixture at 65° C. for 1 hour, and for a further 2–3 hours under cold conditions. To a fixed weight of the polymer-alginate solution, was added and dissolved, an accurate amount of timolol maleate (Huhtamaki OY Pharmaceuticals, Turku, Finland) to make a 0.5% w/w concentration.

EXAMPLE 18

|  | Percentage by weight |
|---|---|
| Timolol maleate | 0.50 |
| Sodium hyaluronate | 1.00 |
| Sodium alginate, high viscosity | 1.00 |
| Sodium borate, decahydrate | 0.19 |
| Boric acid | 1.21 |
| Glycerin | 0.50 |
| Sterile water | 95.60 |

A medicated contact lens was prepared using a suitable glass container in which the sodium borate, boric acid and glycerin were dissolved to make a solution in sterile water. Sodium alginate and sodium hyaluronate were sprinkled into this solution with continuous stirring to form a uniform paste. To a fixed weight of the hyaluronate-alginate mixture, there was added and dissolved an amount of timolol maleate (Huhtamaki OY Pharmaceuticals, Turku, Finland) to make a 0.5% w/w concentration.

An in-vitro evaluation of the contact lens of Examples 16–18 was carried out as follows: The medicated contact lens was prepared by accurately weighing a big drop of the formulation on a glass microscopic slide (2"×1"). Two drops of a 5% by weight calcium chloride counter-ion solution was next placed on the formula drop. After 1 minute, the excess calcium chloride was blotted away from the now formed corneal contact lens.

The glass slide with contact lens in place was next placed at the bottom of the 1 liter dissolution vessel containing 500 ml of purified water, maintained at 37° C. The dissolution experiment was carried out as per method 2 (paddle) of the United States Pharmacopoeia XXII, page 1579, The United States Pharmacopoeial Convention, Mack Publishing Company, 1990. Paddle stirring rate was 50 revolutions per minute.

At regular time intervals, aliquots were removed from the vessels for analysis by High Pressure Liquid Chromatography. Six vessels were used for each formulation (n=6).

TIMOLOL MXLEATE DELIVERY FROM
CORNEAL LENSES n=6

| TIME | CUMULATIVE % OF TIMOLOL RELEASED (SD) | | | | |
|---|---|---|---|---|---|
| | Example 16 | Example 17 | | Example 18 | |
| 0 | 0.0 | 0.0 | | 0.0 | |
| 10 min | 100.0 | — | | — | |
| 30 min | 100.0 | — | | — | |
| 60 min | 100.0 | — | | — | |
| 120 min | — | 80.3 | (12.0) | 77.9 | (6.2) |
| 240 min | — | 90.0 | (3.8) | 93.9 | (2.2 |
| 360 min | — | 90.1 | (3.1) | 94.9 | (2.5) |
| 480 min | — | 95.7 | (3.3) | 97.5 | (2.9) |

It was observed that the drug is released in-vitro, by diffusion and not by the erosion of the lens. Approximately 80% of timolol maleate is released in 1 hour and the remaining amount gradually diffuses out in 3 to 4 hours. The lenses remained intact 48 hours after the start of the experiment. On the other hand, when 0.9% sodium chloride was used in place of purified water as the dissolution medium, the drug was released by both erosion and diffusion, within the first hour. The lenses are first reduced in size and then dissolved away within 6 hours. This erosion is dependent on the replacement of calcium ions (in the lens) with sodium ions (from the dissolution medium). The break up in-vivo is expected to be slow and gradual and is dependent on the sodium concentration in the tear fluid.

In the following examples there are described compositions having multiple uses. For instance, they may be used as vehicles for drug delivery by topical application or by injection or useful as a protective corneal shield or in a process for excimer laser keratectomy as a laser ablatable corneal mask.

The procedure for preparation and the polymeric materials utilized in the composition are those described in Example 1. The TRIS-hydrochloride buffer utilized in this composition was prepared utilizing the ingredients and proportions by weight indicated below.

| TRIS (tromethamine, USP) | 0.6058 |
|---|---|
| Concentrated hydrochloric acid | 0.4123 |
| Purified water, USP | 100 |

The composition was found to have a pH of 7.4 and an osmolality in mOsm/kg of 83. The procedure for preparation of this buffer is as follows: The weighed amount of TRIS was placed in a 2-liter volumetric flask and about 1 liter of purified water was added to the flask. The concentrated hydrochloric acid was added and the solution was made up to volume by adding the remaining water in the formulation.

The calcium based counter-ion solution utilized to gel the inventive drug delivery compositions of Examples 19–22 was prepared utilizing the following proportions of ingredients in proportions by weight.

| Calcium chloride, dehydrate | 1.2 |
|---|---|
| Calcium gluconate, anhydrous | 3.0 |
| Purified water, USP | 100.0 |

The composition had a pH of 6.88 and an osmolality in mOsm/kg of 299. The calcium based counter-ion solution was prepared as follows: The Calcium gluconate and calcium chloride in the required amount were placed in a 200 ml volumetric flask. Approximately 100 ml of water were added to partially dissolve the salts. The solution was, thereafter, warmed to 80° C. to facilitate dissolution. The solution was cooled and the remaining water was added to make up to 200 ml volume.

EXAMPLE 19

A composition containing both sodium alginate and sodium hyaluronate was prepared for use as a vehicle for drug delivery, a laser ablatable corneal mask, a protective corneal shield, or a composition for use in preventing post-surgical adhesions. The proportions by weight are as follows:

| Sodium hyaluronate | 0.5 |
|---|---|
| Sodium alginate | 1.0 |
| Sodium chloride | 0.54 |
| TRIS-hydrochloride Buffer | 97.96 |

The composition was found to have a pH of 7.6 and an osmolality of 297 mosm/kg prior to treatment with calcium ions by the addition of the previously described calcium based counter-ion solution. After treatment with calcium ions the osmolality was 302 mosm/kg.

The product was further characterized by measuring the average penetration in millimeters as determined using a precision penetrometer with a ¼ size (9.38 grams, ASTM D-1043) cone and plunger. The penetration in millimeters prior to treatment of the composition of Example 19 with calcium ions was greater than 20 mm. After treatment with calcium ions the penetration was 4.77 mm.

EXAMPLE 20

A composition containing polyvinyl pyrrolidone and sodium alginate was prepared which is useful for the same applications as that formulation described in Example 19. The proportions in percent by weight of the ingredients of the composition are as follows:

| Polyvinyl pyrrolidone | 0.8 |
|---|---|
| Sodium alginate | 1.0 |
| Sodium chloride | 0.62 |
| TRIS-hydrochloride buffer | 97.58 |

The composition had a pH of 7.59 and an osmolality in mOsm/kg prior to treatment with calcium ions of 320 and after treatment with calcium ions of 289. The penetration utilizing a precision penetrometer as further described in Example 19 was greater than 20 prior to treatment of the composition with calcium ions and 6.57 after treatment with calcium ions.

EXAMPLE 21

A composition useful for the same uses as stated in Example 19 containing a combination of sodium alginate and chondroitin sulfate was prepared.

The proportions of ingredients in percent by weight are as follows:

| | |
|---|---|
| Sodium chondroitin sulfate | 2.0 |
| Sodium alginate | 1.0 |
| Sodium chloride | 0.35 |
| TRIS-hydrochloride buffer | 96.65 |

The composition had a pH of 7.9 and an osmolality expressed in mOsm/kg of 301 prior to treatment with calcium ions and 272 after treatment with calcium ions.

The penetration utilizing a precision penetrometer as further described in Example 19 was found to be greater than 20 mm prior to treatment with calcium counter-ions and 4.57 upon treatment with calcium ions utilizing the calcium counter-ion solution prepared above.

EXAMPLE 22

A composition useful for the same uses as stated in Example 19 containing a combination of hydroxypropyl methyl cellulose, and sodium alginate was prepared. The proportions of ingredients and their percent by weight are as follows:

| | |
|---|---|
| Hydroxypropyl methyl cellulose | 2.0 |
| Sodium alginate | 1.0 |
| Sodium chloride | 0.6 |
| TRIS-hydrochloride buffer | 96.4 |

The composition had a pH of 7.59 and an osmolality expressed in mOsm/kg of 326 prior to treatment with calcium ions and 301 after treatment with calcium ions.

While this invention has been described with reference to certain specific embodiments, it will be recognized by those skilled in the art that many variations are possible without departing from the scope and spirit of the invention, and it will be understood that it is intended to cover all changes and modifications of the invention, disclosed herein for the purposes of illustration, which do not constitute departures from the spirit and scope of the invention.

The embodiments of the invention in which an exclusive property or privilege is claimed are defined as:

1. An aqueous medical device or vehicle useful for drug delivery, a vehicle for the application of a diagnostic agent, a composition for the prevention of post/operative adhesions, a protective corneal shield, or an ablatable corneal shield, said composition characterized as capable of being gelled in situ to produce an hyperosmotic, hypoosmotic, or isoosmotic gel having a buffered pH, said composition comprising at least one ionic polysaccharide, and at least one film forming agent.

2. The composition of claim 1 comprising at least one cross linking agent capable of gelling the ionic polysaccharide.

3. The composition of claim 1 comprising a cross-linking agent having more than one functional group wherein the functional group is selected from the group consisting of chemical and ionic functional groups.

4. The composition of claim 1 wherein cross-linking is accomplished by physical reaction among appropriate functional groups of the polymers.

5. The composition of claim 1 comprising:

part A) an aqueous vehicle comprising at least one ionic polysaccharide and part B) an aqueous solution comprising a counter-ion capable of gelling said ionic polysaccharide, wherein combining parts A and B results in the conversion of said aqueous liquid vehicle to an aqueous gel vehicle.

6. The composition of claim 1 wherein said aqueous vehicle contains a drug selected from the group consisting of antibacterials, antihistamines and decongestants, antiinflammatories, antiparasitics, miotics and anticholinergics, antivirals, local anesthetics, antifingals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives and muscle relaxants, and diagnostics.

7. The composition of claim 1 wherein said film forming polymer is water soluble and selected from the group consisting of the alkyl and hydroxyalkyl methyl celluloses, hyaluronic acid, sodium chondroitin sulfate, polyacrylic acid, polyacrylamide, polycyanolacrylates, alkyl and hydroxyalkyl methacrylate polymers, cyclodextrin, polydextrose, dextran, gelatin, polygalacturonic acid, polyvinyl alcohol, polyvinyl pyrrolidone, polyalkylene glycols, and polyethylene oxide.

8. The composition of claim 1 wherein said ionic polysaccharide is carboxymethylcellulose.

* * * * *